United States Patent [19]
Zhang

[11] Patent Number: 5,692,937
[45] Date of Patent: Dec. 2, 1997

[54] COHESIVE STRETCH BANDAGES

[75] Inventor: Tianhong Zhang, Rockport, Me.

[73] Assignee: Century International Adhesives and Coatings Corporation, Inc., Columbus, Ohio

[21] Appl. No.: 780,460

[22] Filed: Jan. 8, 1997

Related U.S. Application Data

[63] Continuation-in-part of Ser. No. 559,844, Nov. 20, 1995, Pat. No. 5,616,400.

[51] Int. Cl.$^6$ ................................................ C09J 7/02
[52] U.S. Cl. ............................... 442/149; 428/355 N
[58] Field of Search ......................... 442/149, 151; 428/355 N

[56] References Cited

U.S. PATENT DOCUMENTS

| | | | |
|---|---|---|---|
| 4,105,025 | 8/1978 | Wang | 128/90 |
| 4,540,633 | 9/1985 | Kucera | 428/423.1 |
| 4,623,416 | 11/1986 | Henning | 156/331.7 |
| 4,851,459 | 7/1989 | Ramalingam | 523/414 |
| 4,861,826 | 8/1989 | Hummerich | 524/839 |
| 4,880,416 | 11/1989 | Horiuchi | 604/307 |
| 4,889,884 | 12/1989 | Dust | 524/314 |
| 4,902,370 | 2/1990 | Dust | 156/327 |
| 5,230,701 | 7/1993 | Meyer | 602/76 |
| 5,334,690 | 8/1994 | Schafheutle | 528/71 |

*Primary Examiner*—Jenna Davis
*Attorney, Agent, or Firm*—Carroll F. Palmer

[57] ABSTRACT

Cold-seal adhesives are disclosed that contain no natural rubber and are capable of forming dry content on stretchable fabric strips which adhere to one another with acceptable strength at room temperature by pressure contact to form cohesive surgical bandages, but also allow such strips to be reeled into rolls and stored for extended periods of time without blocking. Such cold-seal adhesives are aqueous dispersions having a Zahn Cup #2 viscosity between 16–40 seconds containing 30 to 50 percent solids content of a polyurethane ionomer reaction product of 50–80% polyester polyol, 15–25% aliphatic diisocyanate and 3–6% dimethylol propionic acid neutralized with a base selected from tertiary amines and alkali metal hydroxides and the reaction product possesses a $T_g$ of between about −20° to 5° C.

4 Claims, 1 Drawing Sheet

COHESIVE STRETCH BANDAGES

REFERENCE TO RELATED APPLICATION

This application is a continuation-in-part of U.S. patent application Ser. No. 08/559,844 filed Nov. 20, 1995 now U.S. Pat. No. 5,616,400.

BACKGROUND OF THE INVENTION

1. Field of the Invention

This application relates broadly to cold-seal adhesives, methods of forming adhesive bandages therewith and cohesive stretch bandages comprising the new cold-seal adhesives. More particularly, it concerns (a) polyurethane containing aqueous dispersion adhesives capable of forming dry, non-blocking adhesive layers on stretchable fabric webs that can then later be pressure bonded together without use of heat, (b) cold-sealable stretchable fabric webs comprising such adhesive layers and (c) cohesive stretch bandages comprising the polyurethane containing adhesives.

2. Description of the Prior Art

Cold-seal adhesives are an established class of commercial adhesives characterized by being coated onto plastic films or other substrates to form layers that have the capability of strongly bonding to themselves when pressure is applied, but lacking adhesion to low energy surfaces, e.g., plastic films, coated papers, etc., so such flexible webs bearing these cold-seal adhesives layers may be formed into rolls without blocking, i.e., without sticking together. The technical literature contains information about cold-seal adhesives which have become a recognized commercial commodity, e.g., see U.S. Pat. Nos. 4,810,745, 4,859,521, and 4,902,370.

Natural rubber remains a major component of choice for the production of cold-seal adhesives in spite of disadvantages associated with natural rubber latex, including age discoloration, unpleasant odor, undesirable foaming in wet form and possibility of anaphylactic shock due to presence of natural latex proteins. To overcome the problems associated with natural rubber, synthetic polymer dispersions have been used to replace it in cold-seal adhesive formulations as shown by U.S. Pat. Nos. 4,889,884 & 4,902,370. While limited success has been accomplished in mitigating the aforementioned problems, the fundamental balance of satisfactory cohesive bond strength vs antiblocking properties desired in cold-seal adhesives has proven hard to achieve on a commercial basis without use of natural rubber.

The present invention provides new forms of cold seal adhesives with remarkable balance of satisfactory cohesive bond strength vs antiblocking properties without use of natural rubber as an essential component.

Aqueous polyurethane dispersions are a known class of polymer systems as are various methods for their production and their use as coatings and adhesives, as shown by U.S. Pat. Nos. 4,623,416 & 4,851,459. The present invention builds on this prior knowledge to advance the art in production of cold-seal adhesives and their utilization in cold-sealable stretchable fabric webs, particularly, cohesive stretch bandages made therefrom.

Stretch bandages are established commercially available articles of manufacture on which considerable research and development work has occurred as shown by U.S. Pat. Nos. 5,133,199, 5,307,927, 5,382,445, 5,405,643, 5,449,550, 5,455,060 and 5,498,232. The present invention provides further improvements in this type of article.

OBJECTS

A principal object of the invention is the provision of new forms of polyurethane based, aqueous dispersions capable of forming cold-seal adhesive layers on substrates that possess a commercially acceptable balance of cohesiveness and antiblocking quality.

Further objects include the provision of:

1. Unique methods for production of such polyurethane based, aqueous dispersions.
2. Cold-seal adhesives in the form of aqueous dispersions that are devoid of problems associated with known cold-seal adhesives based on natural rubber latex.
3. Such cold-seal adhesives which in the form of a dry layer exhibit excellent antiblocking properties toward low energy plastic films or webs, but still are capable of forming a strong cohesive bond between themselves under commercially acceptable pressure application.
4. New forms of cohesive stretch bandages.
5. Non-blocking rolls of stretchable fabric strips useful in forming surgical bandages comprising cohesive overlappings thereof.
6. Unique adhesive aqueous dispersions that can be compounded with commercially available aqueous dispersions including acrylic polymer dispersions, vinyl polymer dispersions, synthetic elastomer dispersions, tackifiers, antiblocking agents, etc. to enhance specific properties or requirements.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects are accomplished in accordance with the invention by the provision of a cold-seal adhesive composition in the form of an aqueous dispersion having a Zahn Cup #2 viscosity between 16–40 seconds containing 30 to 50 percent solids content of a polyurethane ionomer reaction product of 50–80% polyester polyol, 15–25% aliphatic diisocyanate and 3–6% dimethylol propionic acid neutralized with a base selected from tertiary amines and alkali hydroxides. The reaction product possesses a $T_g$ of between about −20° to 5° C.

The invention further provides unique stretchable fabric webs comprising a continuous mesh fabric bearing dry cold seal adhesive consisting essentially of a polyurethane ionomer as described above.

Additionally, the invention provides new cohesive stretch bandages free of causing anaphylactic shock to persons using the bandages.

Polyester polyols used in accordance with the invention are commercially available polyester polyols per se or with an optional minor amount of polyether polyol, namely, a mixture containing about 0–20% polyether polyol and 80–100% polyester polyol, used in forming the polyurethane ionomer reaction product.

Preferred polyester polyols include the condensation products of diethylene glycol or dipropylene glycol with adipic acid or adipic acid with an optional amount of phthalic acid (up to 30% based upon the total weight of the mixture), e.g., poly(diethylene glycol adipate). Their average molecular weights range from 500 to 4000, especially 1000–3000.

Preferred polyether polyols include polypropylene glycol and ethylene oxide end capped polypropylene glycol with an average molecular weight from 500 to 4000, especially 1000–3000.

Preferred diisocyantes include hydrogenate methylene dihpenyl diisocyante (HMDI), hexamethylene diisocyanate (HDI), and, especially, isophorene diisocyanate (IPDI).

Preferred neutralization bases include triethanolamine, triethylamine and potassium hydroxide. The mechanical strength of the dry cold-seal adhesive films (coatings) of the invention varies with the base used for neutralization with KOH yielding the strongest films.

The aqueous dispersions of polyurethane prepolymers formed as precursors to the adhesive polyurethane ionomer reaction products of the invention are chain extended with water or the combination of water and a multifunctional aliphatic amine chain extender with 2–4 primary and secondary nitrogen atoms and 2–20 carbon atoms. Such amine chain extenders include ethylene diamine, 1,4-butanediamine, isophorene diamine, triethylenetetraamine, and triethylene oxide diamine (Huntsman EDR 148). Preferably, the quantity of the chain extender reagent is between about 0 to 2% of the total quantity of components used to form the polyurethane ionomer.

The new polyurethane ionomers may be compounded with commercially available aqueous dispersions including acrylic polymer dispersions, vinyl polymer dispersions, synthetic elastomer dispersions, tackifiers, antiblocking agents, etc. to enhance specific properties or requirements. Preferred compositions contain acrylic polymer dispersions with a $T_g$ of between about −50° to −20° C. and a solids content of 45% to 65% by weight. Such acrylic polymers are added to the polyurethane ionomers so the combined composition contains between 5–30% of the acrylic polymer dispersion. The addition of the acrylic polymers and equivalent other polymers to the polyurethane ionomers dispersions of the invention serves to enhance the cohesive quality of films formed from the mixed dispersions without increasing the adhesiveness toward other substrates.

In preferred embodiments, the cold seal adhesive coating in the new stretchable fabric webs is the dried residue from the application to the web of an aqueous cold seal adhesive dispersion as described above.

Important new products of the invention are non-blocking rolls of stretch bandage bearing dry cold seal adhesive as described above.

Typically, the new polymer systems of the invention, are applied to a continuous web of stretchable mesh fabric, e.g., by saturation application, roller coating or spraying both sides. Such adhesive bearing mesh webs after thorough drying can be rolled up for storage and transportation without blocking. Eventually, such coated substrates can be sealed together by overlapping layers of the mesh webs and applying pressure to give good contact with formation of cohesive bonding between the exposed cold-seal adhesive present thereon.

BRIEF DESCRIPTION OF THE DRAWINGS

A more complete understanding of the invention can be obtained by reference to the accompanying drawings in which generic parts of the illustrated matter are indicated by arrowhead lines associated with the designation numerals while specific parts are indicated with plain lines associated with the numerals and wherein.

DESCRIPTION OF THE PREFERRED EMBODIMENTS

Figure 1:
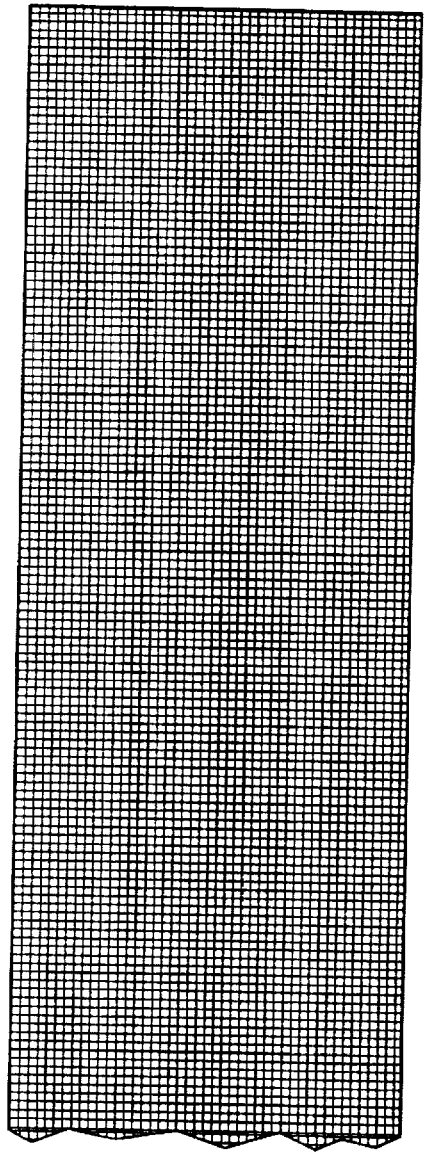
FIG. 1 is a plan view of a section of a cohesive stretch bandage formed in accordance with the invention.
Figure 2:
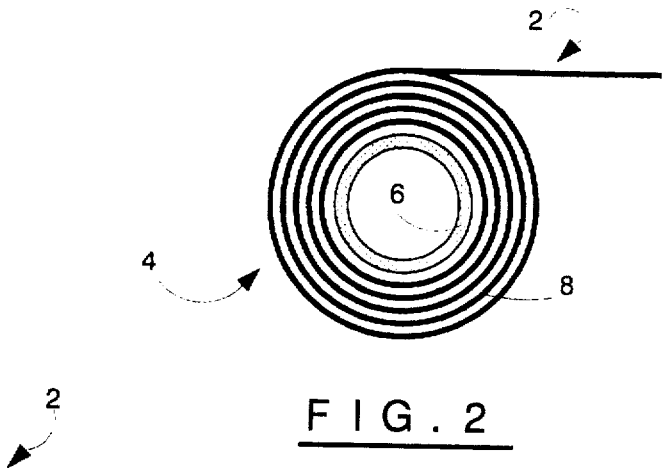
FIG. 2 is a lateral view of a roll of cohesive stretch bandage of the invention.
Figure 3:
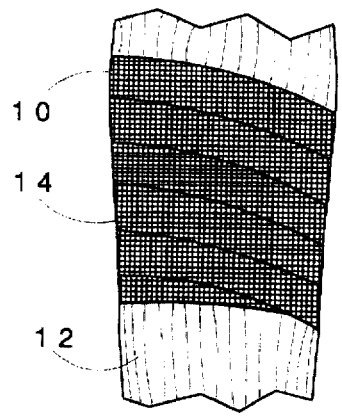
FIG. 3 is a fragmentary lateral view of a limb of a person bandaged with cohesive stretch bandage of the invention.

This invention is illustrated by the following examples of production of cold-seal adhesives and their utilization in accordance therewith. Such examples are for the purpose of illustration and are not intended to limit the scope of the invention unless otherwise specifically indicated. In these examples and throughout the remainder of this specification and the appended claims, all parts are by weight and all percentages are by weight of the total weight of all combined components.

EXAMPLE 1

To a heat-jacketed reactor equipped with agitator, temperature controller and nitrogen in/outlet, 300 parts of poly (diethylene glycol adipate) (Ruco S-1011-55, hydroxyl no. 55), 69.4 parts of isophorene diisocyanate (IPDI, Huls) and 0.1 part of dibutyltin dilaurate are charged under nitrogen purge. This reaction mixture is heated to 85° C. and stirred for one hour, followed by the addition of 13.4 parts of dimethylol propionic acid and 0.1 part of dibutyltin dilaurate. The reaction is then continued at 85° C. for another 5 hours to reach a NCO content about 1.5%. At such point, heating is stopped and 10.1 parts of triethylamine amine is added to the reactor with stirring continued for 10 minutes to neutralize the viscous, anhydrous reaction product. Then, 600 parts of water is added to the reactor with vigorous stirring over a period of 30 minutes forming an aqueous dispersion of the polyurethane ionomer. Final stirring for two hours yields a bluish color, translucent aqueous dispersion containing about 40% solids with a pH of 7.5 and a Zahn No. 2 cup viscosity of 20 seconds.

EXAMPLE 2

To a heat-jacketed reactor equipped with agitator, temperature controller and nitrogen in/outlet, 300 parts of Ruco S-1022-55, 74.9 parts of isophorene diisocyanate (IPDI, Huls) and 0.1 part of dibutyltin dilaurate are charged under nitrogen purge. This reaction mixture is heated to 85° C. and stirred for one hour, followed by the addition of 16.1 parts of dimethylol propionic acid and 0.1 part of dibutyltin dilaurate. The reaction is then continued at 85° C. for another 5 hours to reach a NCO content about 1.6%. At such point, the viscous polymer melt is transferred to 600 parts of water containing 17.8 parts of triethanolamine under vigorous stirring for 30 minutes to form an aqueous dispersion. Then, 4.5 parts of triethylene oxide diamine (Huntsman EDR 148) is added to the dispersion and stirring is continued for another two hours. The final aqueous ionomer dispersion is milky white in color containing about 40% solids with a pH of 7.7 and a Zahn No. 2 cup viscosity of 30 seconds.

EXAMPLE 3

A dispersion composition is prepared by mixing together 70 parts of the aqueous ionomer dispersion of Example 2 and 30 parts of acrylic polymer dispersion containing 50% acrylic polymer having a $T_g$ of −30° C.

EXAMPLE 4

A dispersion composition is prepared by mixing together 70 parts of the aqueous ionomer dispersion of Example 2 and 5 parts of acrylic polymer dispersion containing 60% acrylic polymer having a $T_g$ of −20° C.

EXAMPLE 5

The dispersions of Example 1, 3 & 4 are applied to a continuous two inch wide stretchable strip of knit cotton yarn by immersion saturation which are then oven dried at a temperature range of 90°–95° C. The resulting dry strips 2 are rolled into firm rolls 4 around cores 6.

The rolls 4 are handled and stored under commercial transport and handling conditions without blocking of individual layer 8 in the rolls 4.

Bandages 10 are readily formed on limbs 12 of persons by cutting a suitable length of strip 2 from a roll 4 and winding it about the limb 12. The strip 2 is easily unrolled from the roll 4, but the strip 2 when applied to the limb 12 exhibits sufficient cohesion between separate layers 14 of the bandage 10 to maintain layers in a locked condition relative to one another.

I claim:

1. A cohesive stretch bandage comprising a continuous stretchable fabric web bearing dry cold seal adhesive consisting essentially of a polyurethane ionomer reaction product of 50–80% polyester polyol, 15–25% aliphatic diisocyanate and 3–6% dimethylol propionic acid neutralized with a base, said reaction product possessing a $T_g$ of between about –20° to 5° C.

2. A non-blocking roll of a stretchable fabric strip for construction of surgical bandages comprising a continuous flexible stretchable mesh fabric web bearing dry cold seal adhesive consisting essentially of a polyurethane ionomer reaction product of 50–80% polyester polyol, 15–25% aliphatic diisocyanate and 3–6% dimethylol propionic acid neutralized with a base, said reaction product possessing a $T_g$ of between about –20° to 5° C.

3. A cohesive stretch bandage comprising a continuous stretchable fabric web bearing dry cold seal adhesive comprising 70 to 95% of a polyurethane ionomer reaction product of 50–80% polyester polyol, 15–25% aliphatic diisocyanate and 3–6% dimethylol propionic acid neutralized with a base, said reaction product possessing a $T_g$ of between about –20° to 5° C. and 5 to 30% of an aqueous dispersion containing 45% to 65% acrylic polymer possessing a $T_g$ of between about –50° to –20° C.

4. A non-blocking roll of a stretchable fabric strip for construction of surgical bandages comprising a continuous flexible stretchable mesh fabric web bearing dry cold seal adhesive comprising 70 to 95% of a polyurethane ionomer reaction product of 50–80% polyester polyol, 15–25% aliphatic diisocyanate and 3–6% dimethylol propionic acid neutralized with a base, said reaction product possessing a $T_g$ of between about –20° to 5° C. and 5 to 30% of an aqueous dispersion containing 45% to 65% acrylic polymer possessing a $T_g$ of between about –50° to –20° C.

* * * * *